United States Patent [19]

Nomura et al.

[11] Patent Number: 5,880,294
[45] Date of Patent: Mar. 9, 1999

[54] D-PENTOFURANOSE DERIVATIVES AND PROCESS FOR PREPARING THE SAME

[75] Inventors: Makoto Nomura, Iruma; Hideki Kazuno, Hanno; Tsutomu Sato, Hanno; Masato Washinosu, Hanno; Motoaki Tanaka, Tokorozawa; Akira Matsuda, Sapporo; Tetsuji Asao, Tokorozawa, all of Japan

[73] Assignee: Taiho Pharmaceutical Co., Ltd., Tokyo, Japan

[21] Appl. No.: 981,814

[22] PCT Filed: Apr. 24, 1997

[86] PCT No.: PCT/JP97/01427

§ 371 Date: Jan. 6, 1998

§ 102(e) Date: Jan. 6, 1998

[87] PCT Pub. No.: WO97/43295

PCT Pub. Date: Nov. 20, 1997

[30] Foreign Application Priority Data

May 16, 1996 [JP] Japan ................................ 8-121372

[51] Int. Cl.$^6$ ..................... C07D 307/12; C07D 307/20; C07D 317/44
[52] U.S. Cl. .................. 549/435; 549/438; 549/478
[58] Field of Search ..................... 549/435, 438, 549/478

[56] References Cited

PUBLICATIONS

Rosenthal. A, et al. "Branched–Chain Sugar Nucleosides. Synthesis of 3'–C–Ethyl (And 3'–C–Butyl)Uridine", Carbohydrate Research (1980), vol. 79, pp. 235–242.

*Primary Examiner*—Ba K. Trinh
*Attorney, Agent, or Firm*—Sughrue, Mion, Zinn, Macpeak & Seas, PLLC

[57] ABSTRACT

The present invention relates to D-pentofuranose derivatives represented by the following formulas (1) through (4):

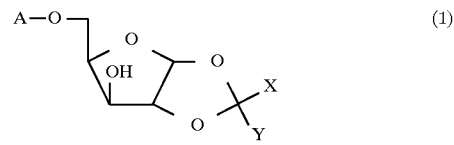

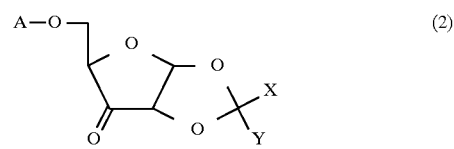

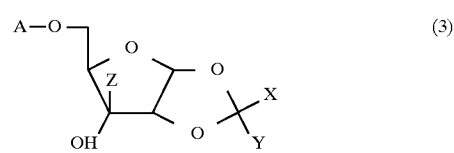

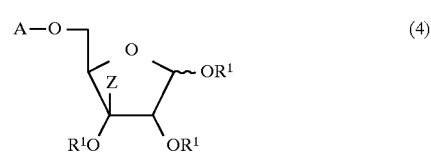

(wherein A represents a chlorobenzoyl group; $R^1$ represents a hydrogen atom, an aliphatic lower acyl group, a substituted or unsubstituted benzoyl group; each of X and Y represents a lower alkyl group; Z represents an ethynyl group or tri-lower alkyl silylethynyl group; the sugar moiety in formula (1) represents xylose; and the sugar moiety of each of formulas (3) and (4) represents ribose). The present invention also relates to a process for preparing the compound (2) characterized by oxidizing the compound of formula (1) with a hypochlorite in the presence of a catalytic amount of 2,2,6,6-tetramethylpiperidinoxy compound, and these compounds are useful as intermediates in the synthesis of 3'-C-substituted ribonucleoside derivatives having excellent antitumor activities.

6 Claims, No Drawings

D-PENTOFURANOSE DERIVATIVES AND PROCESS FOR PREPARING THE SAME

This application is a 371 of PCT/JP97/01427 dated Apr. 24, 1997.

TECHNICAL FIELD

The present invention relates to novel D-pentofuranose derivatives which are useful as industrial synthesis intermediates of 3'-C-substituted ribonucleoside derivatives, and to a process for preparing the same.

BACKGROUND ART

3'-C-Substituted ribonucleoside derivatives represented by the following formula (6):

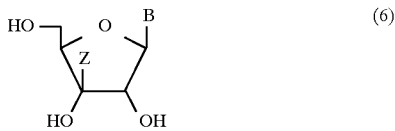

(wherein B represents a nucleic acid base which may have a substituent and Z represents an ethynyl group which may be substituted by a trialkylsilyl group) exhibit excellent antitumor activities, and thus these compounds are useful as antitumor agents (International Patent Application No. PCT/JP95/02554).

Conventionally, 3'-C-substituted ribonucleoside derivatives have been synthesized through nucleophilic addition to 3'-ketonucleoside (Chem. Pharm. Bull., 35, 2605 (1987), Tetrahedron, 47, 1727 (1991)). However, when 3'-ketonucleoside having a protected hydroxyl group at the 5'-position is subjected to nucleophilic addition, nucleosides of the xylose type are mainly formed, and the target ribose type nucleosides can hardly be obtained. Also, Tetrahedron Letters, 36, 10331–1034 (1995) describes that the compound of interest, i.e., 3'-C-substituted ribonucleoside, can be synthesized through nucleophilic addition to 3'-ketonucleoside having unprotected hydroxy at the 5'-position. However, since 5'-O-unsubstituted-3'-ketonucleoside is a very unstable compound, it is not suitable for use as an industrial synthesis intermediate.

Independently, it has been reported that the compound of interest, i.e., a 3'-C-substituted ribonucleoside derivative, can be synthesized through reaction between a 3-C-substituted ribofuranose derivative and a silylated nucleic acid base in an aprotic solvent in the presence of a Lewis acid (International Patent Application No. PCT/JP95/02554). However, this process is not suitable for industrial synthesis of the compound, for it requires a purification procedure by column chromatography because respective intermediates cannot be obtained as crystals. According to this invention, the hydroxyl group at the 3-position of xylofuranose is oxidized to obtain an intermediate 3-ketofuranose, wherein the oxidation step generally includes use of dimethylsulfoxide or chromic acid. In the case of dimethylsulfoxide, dimethylsulfide having foul is generated. Chromic acid is harmful heavy metal that may have adverse effects on the environment. Therefore, neither case is preferred.

Accordingly, the object of the present invention is to provide a stable intermediate for preparing 3'-C-substituted ribonucleoside derivatives industrially and economically, with simplicity and efficiency, without use of a harmful reagent, as well as to provide a process for preparing the intermediate.

DISCLOSURE OF THE INVENTION

Under the above circumstances, the present inventors have conducted careful studies, and have found that D-pentofuranose derivatives represented by the following formulas (1), (2), (3), and (4) are useful intermediates for synthesizing 3'-C-substituted ribonucleoside derivatives, thus leading to completion of the invention.

Accordingly, the present invention is directed to a D-pentofuranose derivative represented by the following formula (1):

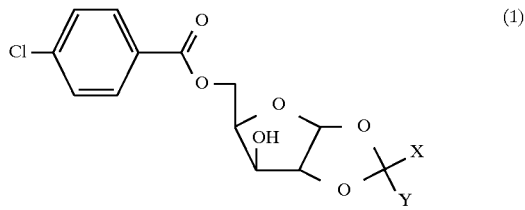

(wherein each of X and Y represents a lower alkyl group and the sugar moiety represents xylose); a D-pentofuranose derivative represented by the following formula (2):

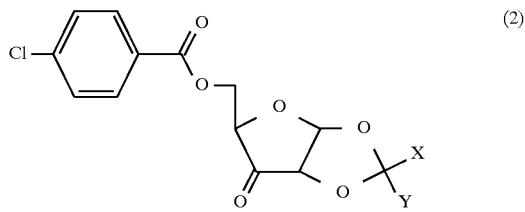

(wherein each of X and Y represents a lower alkyl group); a D-pentofuranose derivative represented by the following formula (3):

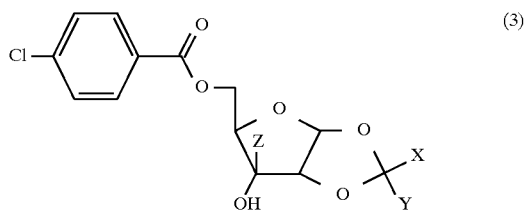

(wherein each of X and Y represents a lower alkyl group, Z represents an ethynyl group which may be substituted by a trialkylsilyl group, and the sugar moiety represents ribose); and to a D-pentofuranose derivative represented by the following formula (4):

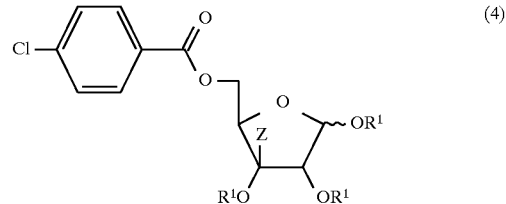

(wherein $R^1$ represents a hydrogen atom, an aliphatic lower acyl group, a substituted or unsubstituted benzoyl group, or a lower alkyloxycarbonyl group, Z represents an ethynyl group which may be substituted by a trialkylsilyl group, and the sugar moiety represents ribose).

The present invention is also directed to a process for preparing a D-pentofuranose derivative of the aforementioned formula (2), which process comprises oxidizing a D-pentofuranose derivative of the aforementioned formula (1) with a hypochlorite in the presence of a catalytic amount of a compound of the following formula (5):

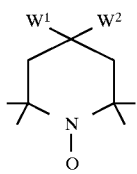

(wherein each of $W^1$ and $W^2$ which may be identical to or different from each other, represents a hydrogen atom or a lower alkoxy group, or $W^1$ and $W^2$ may be linked to each other to represent an oxo group).

BEST MODES FOR CARRYING OUT THE INVENTION

In formulas (1), (2), and (3), examples of the lower alkyl groups represented by X and Y include C1–C6 linear or branched alkyl groups, and specifically, mention may be given of methyl, ethyl, n-propyl, isopropyl, n-butyl, isobutyl, sec-butyl, tert-butyl, pentyl, and hexyl. Of these groups, methyl and ethyl are preferred, with methyl being more preferred.

In formulas (3) and (4), examples of the ethynyl group represented by Z which may be substituted by a trialkylsilyl group include 2-tri(C1–C6)alkylsilylethynyl groups such as 2-trimethylsilylethynyl, 2-triethylsilylethynyl, and ethynyl. Of these groups, ethynyl, 2-trimethylsilylethynyl, and 2-triethylsilylethynyl are preferred, with ethynyl and 2-trimethylsilylethynyl being particularly preferred.

In formula (4), examples of the aliphatic lower acyl group represented by $R^1$ include C1–C6 linear or branched aliphatic lower acyl groups such as formyl, acetyl, propionyl, butyryl, isobutyryl, pivaloyl, pentanoyl, and hexanoyl. Of these groups, acetyl, propionyl, and isobutyryl are preferred, with isobutyryl being particularly preferred.

Examples of the substituted or unsubstituted benzoyl group include a benzoyl group, a halogenobenzoyl group, a C1–C6 alkylbenzoyl group, a C1–C6 alkoxybenzoyl group, and a nitrobenzoyl group. Of these groups, a benzoyl group, a 4-chlorobenzoyl group, and a 4-toluoyl group are preferred, with a benzoyl group and a 4-toluoyl group being more preferred.

Examples of the lower alkyloxycarbonyl group include C2–C7 linear or branched alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, and hexyloxycarbonyl. Of these groups, methoxycarbonyl and ethoxycarbonyl are preferred, and in particular, ethoxycarbonyl is preferred.

In formula (5), examples of the lower alkoxy groups represented by $W^1$ and $W^2$ include C14 6 linear or branched alkoxy groups such as methoxy, ethoxy, n-propoxy, isopropoxy, n-butoxy, isobutoxy, sec-butoxy, tert-butoxy, pentyloxy, and hexyloxy. Of these groups, methoxy and ethoxy are preferred, with methoxy being more preferred.

The process for preparing the compounds of the present invention will next be described with reference to the following reaction scheme.

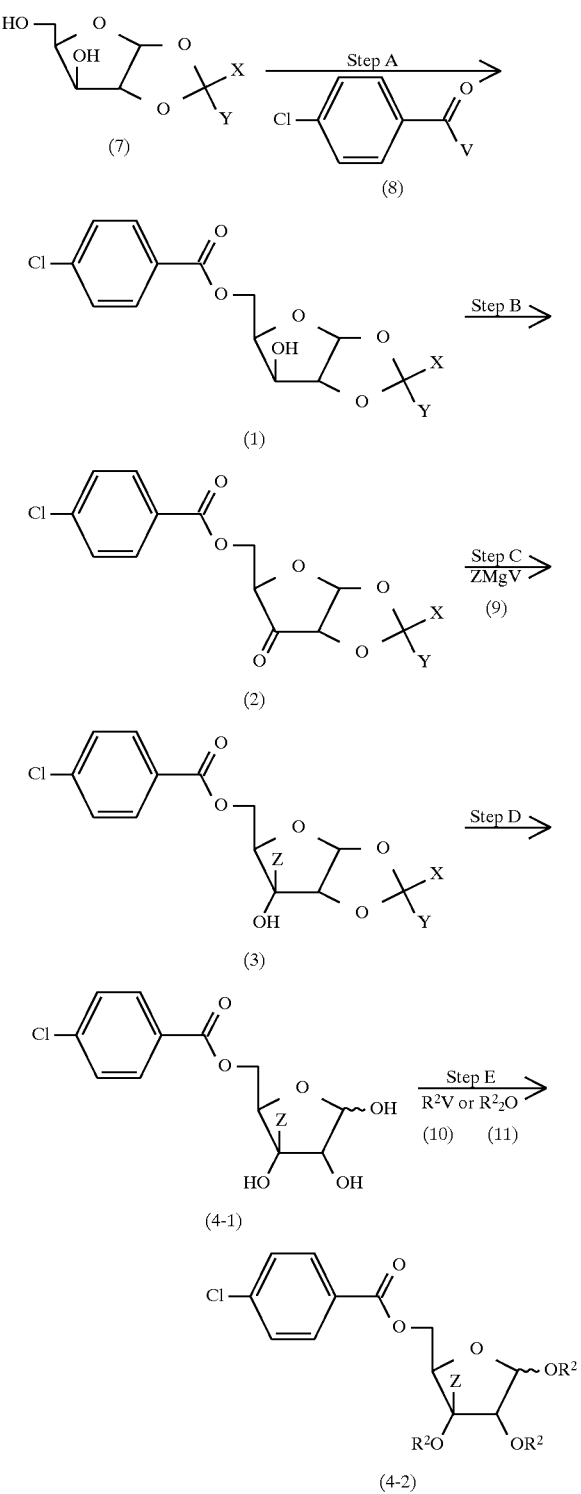

Reaction Scheme 1

(wherein X, Y, and Z have the same meanings as described above, $R^2$ represents an aliphatic lower acyl group, a substituted or unsubstituted benzoyl group, or a lower alkyloxycarbonyl group, and V represents a halogen atom).

(Step A)

In the above reaction scheme, step A represents a process for obtaining a compound of formula (1) through reaction of a conventionally known compound of formula (7) and 4-chlorobenzoyl halide (8) in a suitable solvent in the presence of a base.

In 4-chlorobenzoyl halide (8), examples of the halogen atom represented by V include a fluorine atom, a chlorine atom, a bromine atom, and an iodine atom. Of these, chlorine and bromine are preferred.

Examples of the base used in this step include organic amines such as pyridine, triethylamine, and piperidine, alkali metal hydroxides such as sodium hydroxide and potassium hydroxide, sodium acetate, potassium carbonate, sodium carbonate, and sodium hydrogencarbonate. Of these, preferred are pyridine, triethylamine, potassium carbonate, sodium carbonate, sodium hydrogencarbonate, and more preferred are triethylamine, potassium carbonate, sodium carbonate, and sodium hydrogencarbonate.

The solvent which may be used in this step is not particularly limited so long as it does not affect the reaction adversely. For example, there may be used ethers such as diethyl ether, dimethoxyethane, tetrahydrofuran, and dioxane; halogenated hydrocarbons such as methylene chloride and chloroform; aromatic hydrocarbons such as benzene, toluene, and xylene; acetic acid esters such as methyl acetate and ethyl acetate; and aprotic polar solvents such as N,N-dimethylformamide, dimethylsulfoxide, and acetonitrile. These may be used singly or as a mixture with water.

In order to accelerate the reaction, 0.001–1 equivalent of an organic amine such as 4-dimethylaminopyridine or a similar compound as a catalyst may be added in portion to the compound of formula (7).

In the reaction, preferably 1–5 equivalents, more preferably 1–2 equivalents, of 4-chlorobenzoyl halide with respect to the compound of formula (7) are used. The reaction temperature is from −20° C. to 100° C., preferably 0° C. to 40° C. The reaction time is generally from 0.1 to 10 hours. Preferably, the reaction advantageously proceeds within 10 minutes to 5 hours.

The compound of formula (1) obtained in the above step may or may not be isolated and subsequently used in Step B.

(Step B)

Step B represents a process for obtaining a compound of formula (2) by dissolving the formula (1) compound and a compound represented by formula (5) in a suitable solvent, and reacting the thus-prepared solution with an aqueous solution or a suspension of a hypochlorite that has been adjusted to have a pH of 8–9 with aninorganic salt or inorganic acid.

Examples of the hypochlorites include sodium hypochlorite and calcium hypochlorite.

The solvent which may be used in this step is not particularly limited so long as it does not affect the reaction adversely. For example, there may be used ethers such as diethyl ether, dimethoxyethane, tetrahydrofuran, and dioxane; halogenated hydrocarbons such as methylene chloride and chloroform; aromatic hydrocarbons such as benzene, toluene, and xylene; acetic acid esters such as methyl acetate and ethyl acetate; and aprotic polar solvents such as N,N-dimethylformamide, dimethylsulfoxide, and acetonitrile.

Examples of inorganic salts which may be used in this step include sodium hydrogencarbonate and potassium hydrogencarbonate. Examples of the inorganic acid include hydrochloric acid and sulfuric acid.

In the reaction, preferably 0.0001–1 equivalent, more preferably 0.001–0.1 equivalent, of the formula (5) compound may be used with respect to the formula (1) compound. The hypochlorite is used in an amount of 1–10 equivalents, more preferably 1–3 equivalents, and the inorganic salt or inorganic acid for adjusting pH is used in an amount of 0.5–100 equivalents, preferably 1–5 equivalents.

The reaction temperature is 0° C. to 60° C., preferably 0° C. to 30° C. The reaction time is generally from 1 minute to 10 hours. Preferably, the reaction advantageously proceeds within 10 minutes to 3 hours. The compound of formula (2) obtained in this step may or may not be isolated and subsequently used in Step C.

(Step C)

Step C represents a process for obtaining a compound of formula (3) by causing a reaction between the formula (2) compound and a Grignard reagent represented by ZMgV (9) in a suitable solvent.

The Grignard reagent represented by ZMgV (9) is a compound which is prepared by use of known compounds or known methods. Examples of halogen atoms represented by V include a fluorine atom, a chlorine atom, a bromine atom, and an iodine atom. Of these, a chlorine atom and a bromine atom are preferred.

The solvent which may be used in this step is not particularly limited so long as it is generally used in Grignard reactions. For example, mention may be given of ethers such as diethyl ether, dimethoxyethane, tetrahydrofuran, and dioxane; and aromatic hydrocarbons such as benzene, toluene, and xylene.

In the reaction, preferably 1–10 equivalents, more preferably 1–5 equivalents, of the Grignard reagent may be used with respect to the formula (2) compound. The reaction temperature is −78° C. to 60° C., preferably −20° C. to 30° C. The reaction time is generally from 5 minutes to 50 hours. Preferably, the reaction advantageously proceeds within 30 minutes to 24 hours.

The compound of formula (3) obtained in this step may or may not be isolated and subsequently used in Step D.

(Step D)

Step D represents a process for obtaining a compound of formula (4-1) by hydrolyzing the formula (3) compound in a suitable solvent in the presence of an acidic compound.

Examples of the acidic compound include carboxylic acids such as formic acid and acetic acid; acid anhydrides such as acetic anhydride; acid halides such as acetyl chloride and inorganic acids such as hydrochloric acid, hydrobromic acid, and sulfuric acid.

The solvent which may be used in this step may be water or a mixture of water and an organic solvent. Examples of the organic solvent include ethers such as diethyl ether, dimethoxyethane, tetrahydrofuran, and dioxane; halogenated hydrocarbons such as methylene chloride and chloroform; aromatic hydrocarbons such as benzene, toluene, and xylene; and aprotic polar solvents such as N,N-dimethylformamide, dimethylsulfoxide, and acetonitrile.

In the reaction, preferably 0.1–5,000 equivalents, more preferably 1–2,000 equivalents, of the acidic compound may be used with respect to the formula (3) compound. The reaction temperature is 0° C. to 150° C., preferably 50° C. to 120° C. The reaction time is generally from 10 minutes to 80 hours. Preferably, the reaction advantageously proceeds within 30 minutes to 50 hours.

The compound of formula (4-1) obtained in this step may or may not be isolated and subsequently used in Step E.

(Step E)

Step E represents a process for obtaining a compound of formula (4-2) by causing a reaction between the formula (4-1) compound and an acid halide of formula (10) or an acid anhydride of formula (11) in a suitable solvent in the presence of a base.

In the acid halide of formula (10) and acid anhydride of formula (11), examples of the aliphatic lower acyl group represented by $R^2$ include those previously listed for the aforementioned aliphatic lower acyl group represented by $R^1$.

Examples of the substituted or unsubstituted benzoyl group include those previously listed for the aforementioned substituted or unsubstituted benzoyl group represented by $R^1$.

Examples of the lower alkyloxycarbonyl group include those previously listed for the aforementioned lower alkyloxycarbonyl group represented by $R^1$.

Examples of the acid halide include acetyl chloride, isobutyryl chloride, benzoyl chloride, and p-toluoyl chloride. Examples of the acid anhydride include acetic anhydride, isobutyric anhydride, and benzoic anhydride.

Examples of the base used in this step include organic amines such as pyridine, triethylamine, and piperidine; alkali metal hydroxides such as sodium hydroxide and potassium hydroxide; sodium acetate; potassium carbonate; and sodium carbonate.

The solvent which may be used in this step is not particularly limited so long as it does not affect the reaction adversely. For example, there may be used ethers such as diethyl ether, dimethoxyethane, tetrahydrofuran, and dioxane; halogenated hydrocarbons such as methylene chloride and chloroform; aromatic hydrocarbons such as benzene, toluene, and xylene; acetic acid esters such as methyl acetate and ethyl acetate; alkyl ketones such as acetone and methyl ethyl ketone; and aprotic polar solvents such as N,N-dimethylformamide, dimethylsulfoxide, and acetonitrile. These may be used singly or as a mixture with water.

In order to accelerate the reaction, 0.001–1 equivalent of an organic amine such as 4-dimethylaminopyridine or a similar compound as a catalyst may be added in portion to the compound of formula (4-1).

In the reaction, preferably 1–20 equivalents, more preferably 3–5 equivalents, of the acid halide or acid anhydride with respect to the compound of formula (4-1) are used.

The reaction temperature is from −20° C. to 200° C., preferably 0° C. to 100° C. The reaction time is generally from 0.1 to 50 hours. Preferably, the reaction advantageously proceeds within 30 minutes to 30 hours.

The compounds of the present invention may be isolated and purified by customary means, specifically, by recrystallization, and silica gel column chromatography.

As shown in the below-described reaction scheme, the D-pentofuranose derivative of formula (4-2) obtained through the above steps is transformed into a pharmaceutically useful compound, 3'-C-substituted ribonucleoside (6), through reaction with a silylated nucleic acid base of formula (12) in the presence of a Lewis acid to form an intermediate having good crystallinity and subsequently through a deprotection reaction in the presence of a base.

Reaction Scheme 2:

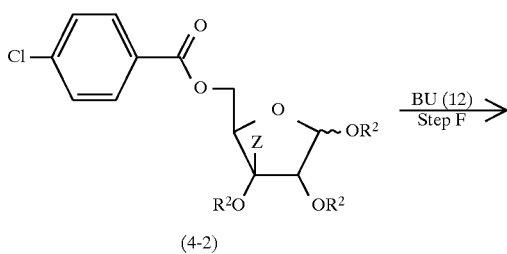

(4-2)

-continued
Reaction Scheme 2:

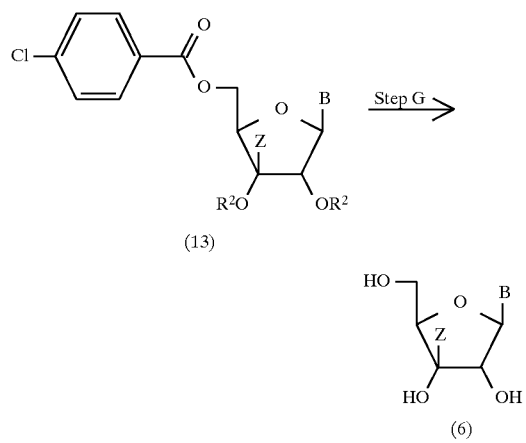

(wherein $R^2$, Z, and B have the same meanings as defined before, and U represents a silyl protective group).

(Step F)

In the above-described reaction scheme 2, Step F represents a process for obtaining a compound of formula (13) by causing a reaction between the D-pentofuranose derivative of the present invention represented by formula (4-2) and the silylated nucleic acid base of formula (12) in a suitable aprotic solvent in the presence of a Lewis acid.

The aforementioned silylated nucleic acid base of formula (12) is a known compound and may be prepared in accordance with the method described by Vorbruggenn et al. in Chem. Ber., 114, 1234 (1981).

As regards the silylated nucleic acid base BU of formula (12), examples of the nucleic acid base represented by B include a pyrimidine base (such as cytosine, thymine, and uracil) and a purine base (such as adenine and guanine); examples of the silyl protective group represented by U include a trimethylsilyl group, a tert-butyldimethylsilyl group, a methyldiisopropylsilyl group, and triisopropylsilyl group.

Examples of the Lewis acid include stanic chloride, trimethylsilyl trifluoromethanesulfonate, aluminum trichloride, and titanium tetrachloride.

The solvent which may be used in this step is not particularly limited so long as it does not affect the reaction adversely. For example, there may be used ethers such as diethyl ether, dimethoxyethane, tetrahydrofuran, and dioxane; halogenated hydrocarbons such as methylene chloride and chloroform; aromatic hydrocarbons such as benzene, toluene, and xylene; alkyl ketones such as acetone and methyl ethyl ketone; and aprotic polar solvents such as N,N-dimethylformamide, dimethylsulfoxide, and acetonitrile.

In the reaction, preferably 1–10 equivalents, more preferably 1–5 equivalents, of the compound of formula (12) and 1–12 equivalents, preferably 1–7 equivalents, of Lewis acid are used with respect to the compound of formula (4-2). The reaction temperature is from 0° C. to 120° C., preferably 10° C. to 90° C. The reaction time is generally from 0.1 to 150 hours. Preferably, the reaction advantageously proceeds within 0.5 to 80 hours.

The compound of formula (13) obtained in this step may or may not be isolated and subsequently used in Step G.

(Step G)

Step G represents a process for obtaining a compound of formula (6) by deprotecting the formula (13) compound in a suitable solvent in the presence of a base.

Examples of the base used in this step include alkali metal hydroxides such as sodium hydroxide and potassium hydroxide; sodium alcoholates such as sodium methoxide and sodium ethoxide; and ammonium derivatives such as triethylamine and ammonia.

The solvent which may be used in this step is not particularly limited so long as it does not affect the reaction adversely. For example, there may be used ethers such as diethyl ether, dimethoxyethane, tetrahydrofuran, and dioxane; halogenated hydrocarbons such as methylene chloride and chloroform; aromatic hydrocarbons such as benzene, toluene, and xylene; acetic acid esters such as methyl acetate and ethyl acetate; alkyl ketones such as acetone and methyl ethyl ketone; and aprotic polar solvents such as N,N-dimethylformamide, dimethylsulfoxide, and acetonitrile; low alkyl alcohol such as methanol and ethanol; and water. These may be used singly or as a mixture.

In the reaction, the basic compound is preferably used in an amount of 0.001–100 mols with respect to the compound of formula (13). The reaction temperature is from 0° C. to 100° C., preferably 0° C. to 70° C. The reaction time is generally from 5 minutes to 100 hours. Preferably, the reaction advantageously proceeds within 15 minutes to 60 hours.

EXAMPLES

Examples of the process for preparing the compounds of the present invention will next be described, and thereafter, examples of processes for preparing 3'-C-trimethylsilylethynylnucleosides and 3'-C-ethynylnucleosides will be given for reference.

Example 1

Preparation of 5-O-(4-chlorobenzoyl)-1,2-O-isopropylidene-α-D-xylofuranose:

1,2-O-isopropylidene-a-xylofuranose (154 g; 810 mmol) and triethylamine (339 ml; 2.43 mol) were dissolved in dichloromethane (1.5 l), and the mixture was cooled to 0° C. 4-Chlorobenzoyl chloride (113 ml; 891 mmol) was added dropwise and the mixture was stirred for 2 hours while being cooled on ice. Saturated aqueous sodium hydrogencarbonate solution (500 ml) was added and phases were separated. The dichloromethane phase was washed twice with water and then once with saturated brine. The dichloromethane phase was dried over magnesium sulfate, and the solvent was evaporated under reduced pressure. The residue was crystallized from n-hexane/chloroform (10:1; 1.6 liters), yielding 196 g (74%) of the title compound as pale yellow powder.

mp: 101°–102° C., FAB-MS: addition of NaI $(M+Na)^+$ $^1$H-NMR(CDCl$_3$)δ: 7.99(2H, d, J=8.8 Hz), 7.44(2H, d, J=8.8 Hz), 5.96(1H, d, J=3.7 Hz), 4.79(1H, dd, J=9.3 Hz, 13.1 Hz), 4.60(1H, d, J=3.7 Hz), 4.37–4.41(2H, m), 4.18 (1H, brs), 3.05(1H, d, J=3.9 Hz, exchanged with D$_2$O), 1.51(3H, s), 1.33(3H, s)

Example 2

Preparation of 5-O-(4-chlorobenzoyl)-1,2-O-isopropylidene-α-D-erythropentofuranose-3-urose:

5-O-(4-Chlorobenzoyl)-1,2-O-isopropylidene-α-D-xylofuranose (195 g; 593 mmol) and 2,2,6,6-tetramethylpeperidinoxy (937 mg; 5.93 mmol) were dissolved in dichloromethane (990 ml), and the mixture was cooled on ice. A mixture of aqueous sodium hypochlorite solution (336 ml; 8.5–13.5% active chlorine), sodium hydrogencarbonate (112 g), and water (1.9 liters) was poured at a single time, and the mixture was stirred for 30 minutes on ice. 2-Propanol (19.5 ml) was added to the reaction mixture, followed by stirring for 10 minutes and separating phases. The dichloromethane phase was washed twice with water, dried over magnesium sulfate, and then subjected to filtration. The filtrate was evaporated and the residue was crystallized from n-hexane-chloroform (10:1) (1.6 liters). The precipitated crystals were collected by filtration, yielding 171 g (88%) of the title compound as white powder.

mp: 111°~112° C.

FAB-MS: $327(M+H)^+$ $^1$H-NMR(CDCl$_3$)67: 7.89(2H d J=8.5 Hz), 7.42(2H d, J=8.5 Hz). 6.12(1H, d, J=4.4 Hz), 4.68–4.73(2H, m), 4.46(1H, dd, J=5.1 Hz, 13.1 Hz), 4.41 (1H, d, J=4.4 Hz), 1.52(3H, s), 1.44(3H, s)

Example 3

Preparation of 5-O-(4-chlorobenzoyl)-3-C-(2-trimethylsilylethynyl)-1,2-isopropylidene-α-D-ribofuranose:

Trimethylsilylacetylene (8.8 ml; 62.3 mmol) was dissolved in tetrahydrofuran (120 ml) under argon atmosphere, and the mixture was stirred at 0° C. To the resultant solution was added dropwise a solution (65.8 ml; 61.2 mmol) of 0.93M ethylmagnesium bromide over 7 minutes. The mixture was stirred for 1 hour on ice. Subsequently, 5-O-(4-chlorobenzoyl)-1,2-O-isopropylidene-α-D-erythropentofuranose-3-urose (10.0 g; 30.6 mmol) dissolved in tetrahydrofuran (60 ml) was added dropwise, and stirring was continued for an additional three hours. Aqueous 1N ammonium chloride solution (120 ml) was added to the reaction mixture, and the liquid temperature was returned to room temperature. Following separation of phases, the tetrahydrofuran phase was washed with saturated aqueous sodium chloride solution (200 ml×2), dried over magnesium sulfate, and then subjected to filtration. The filtrate was evaporated and the residue was crystallized from methanol-water (1:1) (120 ml). The thus-obtained yellow crude product of the title compound was dried under reduced pressure and suspended in n-hexane (200 ml). The suspension was stirred for 1 hour at room temperature. Crystals were collected by filtration, yielding 6.94 g (53%) of the title compound as white powder.

mp: 130°~132° C.

EI-MS: $425(M)^+$ $^1$H-NMR(CDCl$_3$)δ: 8.02(2H d, J=8.5 Hz), 7.41(2H, d, J=8.5 Hz), 5.95(1H, d, J=3.9 Hz), 4.74(1H, dd, J=3.6 Hz, 12.0 Hz), 4.17(1H, d, J=3.9 Hz), 4.53(1H, dd, J=7.8 Hz, 12.0 Hz), 4.17(1H, dd, J=3.6 Hz, 7.8 Hz). 2.93(1H, s, exchanged with D$_2$O), 1.60(3H, s), 1.39(3H, s), 0.19(9H, s)

Example 4

Preparation of 5-O-(4-chlorobenzoyl)-3-C-ethynyl-1,2-O-isopropylidene-α-D-ribofuranose:

The 5-O-(4-chlorobenzoyl)-1,2-O-isopropylidene-α-D-erythropentofuranose-3-urose (6.52 g; 20.0 mmol) obtained in Example 2 was dissolved in tetrahydrofuran (26 ml) in an argon atmosphere and the mixture was stirred at 0° C. To the resultant solution was added dropwise a solution (50.0 ml; 25.0 mmol) of 0.5M ethynylmagnesium bromide. The mixture was stirred for 40 minutes on ice. Subsequently, aqueous 15% ammonium chloride solution (16 ml) was added to the reaction mixture, and the liquid temperature was returned to room temperature. Following separation of phases, the tetrahydrofuran phase was washed with 25% aqueous sodium chloride solution (16 ml×1). The solvent was evaporated and the residue was dissolved in isopropanol (15 ml). The solution was added dropwise to water (15 ml) for crystallization. The precipitated crystals were collected by filtration, yielding 6.28 g (89%) of the title compound as white powder.
mp: 136°–137° C.
FAB-MS: addition of KI, 391 (M+K)$^+$
$^1$H-NMR(CDCl 3) δ: 8.01(2H, d, J=8.6 Hz), 7.41(2H, d, J=8.6 Hz), 5.95(1H, d, J=3.6 Hz), 4.55–4.76(3H, m), 4.15–4.20(1H, m), 3.01(1H, brs), 2.65(1H, s), 1.61(3H, s), 1.46(3H, s)

Example 5

Preparation of 5-O-(4-chlorobenzoyl)-3-C-(2-trimethylsilylethynyl)-D-ribofuranose:

The 5-O-(4-chlorobenzoyl)-3-C-(2-trimethylsilylethynyl)-1,2-isopropylidene-α-D-ribofuranose (20.0 g; 47.1 mmol) obtained in Example 3 was suspended in a mixture of acetic acid (320 ml) and water (80 ml), and the mixture was refluxed for 13 hours at 100° C. The resultant solution was cooled, and the solvent was evaporated under reduced pressure. The residue was dissolved in methanol (150 ml). Water (180 ml) was added with stirring. The precipitated crystals were collected by filtration, yielding 12.0 g (yield: 66.2%) of the title compound as white powder.
mp: 130°–132° C.
FAB-MS: 385 (M+H)$^+$
$^1$H-NMR(CDCl$_3$) δ: 7.98(2H, d, J=8.5 Hz), 7.43(2H, d, J=8.5 Hz), 5.47–5.51(1H, dd, J=4.4 Hz, 8.7 Hz), 4.46–4.63 (3H, m), 4.24(1H, dd, J=4.4 Hz, 6.8 Hz), 3.58(1H, d, J=6.8 Hz), 3.13(1H, s), 3.07(1H, d, J=8.7 Hz), 0.15(9H, s)

Example 6

Preparation of 5-O-(4-chlorobenzoyl)-3-C-ethynyl-D-ribofuranose:

The 5-O-(4-chlorobenzoyl)-3-C-ethynyl-1,2-O-isopropylidene-α-D-ribofuranose (30.0 g; 85.0 mmol) obtained in Example 4 was dissolved in a mixture of acetic acid (480 ml) and water (120 ml), and the mixture was refluxed for 4 hours. The reaction mixture was cooled, and the solvent was evaporated under reduced pressure. Water (150 ml) was added to the residue and the mixture was stirred for 3 hours at room temperature. The precipitated crystals were collected by filtration. Dry crude crystals were suspended in isopropyl ether, and the suspension was stirred for 30 minutes. The crystals were collected by filtration and dried under reduced pressure, yielding 17.3 g (yield: 65.1%) of the title compound as white powder.
mp: 116°–117.5° C.
FAB-MS: addition of KI, 351 (M+K)$^+$
$^1$H-NMR(CDCl$_3$) δ: 7.98(2H, d, J=8.8 Hz), 7.43(2H, d, J=8.8 Hz), 5.47–5.51(1H, m) 4.50–4.68(3H, m), 4.26(1H, t, J=4.9 Hz) 3.69(1H, d, J=8.3 Hz), 3.34(1H, s), 3.19(1H, d, J=4.9 Hz), 2.66(1H, s)

Example 7

Preparation of 1,2,3,5-O-tetra-(4-chlorobenzoyl)-3-C-(2-trimethylsilylethynyl)-α,β-D-ribofuranose:

The 5-O-(4-chlorobenzoyl)-3-C-(2-trimethylsilylethynyl)-D-ribofuranose (22 g; 57.2 mmol) obtained in Example 5 and 4-dimethylaminopyridine (210 mg; 1.72 mmol) were dissolved in dichloromethane (280 ml). To the resultant solution was added triethylamine (33.5 ml; 240 mmol), and the mixture was cooled on ice. Subsequently, 4-chlorobenzoyl chloride (29.1 ml; 229 mmol) was added to the reaction mixture, and the liquid temperature was returned to room temperature. The mixture was stirred for one hour. Water (220 ml) was added, and the mixture was stirred for 15 minutes, followed by separation of phases. The dichloromethane phase was washed twice with water, once with saturated sodium hydrogencarbonate solution, and further with water once. The dichloromethane phase was dried over magnesium sulfate. After filtration, the filtrate was evaporated under reduced pressure. Isopropyl ether (100 ml) was added to the residue, and the insoluble matter was removed by filtration. The filtrate was evaporated, and the residue was dissolved in ethanol (800 ml). The resultant ethanol solution was added to water (1.1 liters) with stirring at room temperature. The precipitated powder was collected by filtration and dried under reduced pressure, yielding 39.9 g (yield: 87%) of the title compound as pale yellow powder.
mp: 67°–69° C.
FAB-MS: addition of NaI, 823 (M+Na)$^+$
$^1$H-NMR(DMSO-d$_6$) δ: 7.75–8.07(8H, m), 7.20–7.46(8H, m), 6.92(0.55H, d, J=4.4 Hz), 6.55(0.45H, s), 6.26(0.45H, s), 6.11(0.55H, d, J=4.4 Hz), 4.73–5.09(3H, m), 0.17(4.05H, s), 0.12(4.95H, s)
α-anomer:β-anomer=55:45

Example 8

Preparation of 5-O-(4-chlorobenzoyl)-1,2,3-tri-O-isobutyryl-3-C-(2-trimethylsilylethynyl)-α,β-D-ribofuranose:

The 5-O-(4-chlorobenzoyl)-3-C-(2-trimethylsilylethynyl)-D-ribofuranose (2.00 g; 5.20 mmol) obtained in Example 5 was dissolved in dichloromethane (30 ml). To the resultant solution was added triethylamine (2.10 g; 20.8 mmol). A solution (1 ml) of 4-dimethylaminopyridine (19 mg; 0.16 mmol) in dichloromethane was added thereto, and the mixture was cooled on ice. Subsequently, isobutyryl chloride (2.17 ml; 20.8 mmol) was added to the mixture, and the liquid temperature was returned to room temperature. The mixture was stirred for five hours. Methanol (30 ml) was added to the reaction mixture, and the mixture was stirred for 40 minutes. Dichloromethane (30 ml) and water (50 ml) were added, followed by separation of phases. The aqueous phase was extracted with dichloromethane (30 ml). The dichloromethane phases were combined, washed with 10% aqueous sodium hydrogencarbonate solution twice and 25% aqueous sodium chloride solution once. The dichloromethane phase was dried over magnesium sulfate. After filtration, the filtrate was evaporated under reduced pressure. The residue was purified by silica gel column chromatography (dichloromethane), yielding 2.68 g (yield: 87%) of the title compound as a colorless oily substance.
FAB-MS: addition of KI, 823 (M+K)$^+$
$^1$H-NMR(CDCl$_3$)δ: 8.01–8.05(2H, m), 7.41–7.45(2H, m), 6.52(0.5H, d, J=4.6 Hz), 6.10(0.5H, s), 5.75(0.5H, s), 5.71 (0.5H, d, J=4.6 Hz), 4.57–4.79(3H, m), 2.51–2.65(3H, m), 1.12–1.22(18H, m), 0.15(4.5H, s), 0.09(4.5H, s)
α-anomer:β-anomer=5:5

Example 9

Preparation of 1,2,3-tri-O-benzoyl-5-O-(4-chlorobenzoyl)-3-C-(2-trimethylsilylethynyl)-α,β-D-ribofuranose:

The 5-O-(4-chlorobenzoyl)-3-C-(2-trimethylsilylethynyl)-D-ribofuranose (2.00 g; 5.20 mmol) obtained in Example 5 was dissolved in dichloromethane (30 ml). To the resultant solution was added triethylamine (2.10 g; 20.8 mmol). A solution (1 ml) of 4-dimethylaminopyridine (20 mg; 0.16 mmol) in dichloromethane was added thereto, and the mixture was cooled on ice. Subsequently, benzoyl chloride (2.11 ml; 18.2 mmol) was added to the mixture, and the liquid temperature was returned to room temperature. The mixture was stirred for three hours. Water (25 ml) was added to the reaction mixture, and the mixture was stirred for 30 minutes, then phases were separated. The dichloromethane phase was washed once with water, once with saturated aqueous sodium hydrogencarbonate solution, then once with water. The dichloromethane phase was dried over magnesium sulfate. After filtration, the filtrate was evaporated under reduced pressure. The residue was purified by silica gel column chromatography (dichloromethane) and pulverized from ethanol-water, yielding 2.81 g (yield: 77.5%) of the title compound as colorless powder.

mp: 63°–66° C.

FAB-MS: addition of KI, 735 (M+K)$^+$ $^1$H-NMR (DMSO-d$_6$)δ: 8.11–7.30(19H, m), 6.93(0.6H, d, J=4.6 Hz), 6.60(0.4H, s), 6.15(0.6H, d, J=4.6 Hz), 6.12 (0.4H, s), 5.27(0.6H, t. J=4.1 Hz), 5.21(0.4H, dd, J=6.7 Hz, 5.1 Hz), 4.70–4.92(2H, m), 0.11(3.6H, s), 0.03(5.4H, s) α-anomer:β-anomer=6:4

Example 10

Preparation of 5-O-(4-chlorobenzoyl)-1,2,3-tri-O-(4-toluoyl)-3-C-(2-trimethylsilylethynyl)-α,β-D-ribofuranose:

The 5-O-(4-chlorobenzoyl)-3-C-(2-trimethylsilylethynyl)-D-ribofuranose (1.00 g; 2.60 mmol) obtained in Example 5 was dissolved in dichloromethane (30 ml). To the resultant solution was added triethylamine (1.05 g; 10.4 mmol), 4-Dimethylaminopyridine (10 mg; 0.08 mmol) was added thereto, and the mixture was cooled on ice. Subsequently, 4-toluoyl chloride (1.20 ml; 9.10 mmol) was added to the mixture, and the liquid temperature was returned to room temperature. The mixture was stirred for two hours. Water (20 ml) was added to the reaction mixture, and the mixture was stirred for 40 minutes. Dichloromethane (30 ml) and water (30 ml) were added, followed by separation of phases. The dichloromethane phase was washed once with water, once with 10% aqueous sodium hydrogencarbonate solution, then once with water. The dichloromethane phase was dried over magnesium sulfate. After filtration, the filtrate was evaporated under reduced pressure. The residue was purified by silica gel column chromatography (dichloromethane) and pulverized from ethanol-water, yielding 1.46 g (yield: 76%) of the title compound as colorless powder.

mp: 62.5°–66.0° C.

FAB-MS: addition of KI, 777 (M+K)$^+$ $^1$H-NMR(DMSO-d$_6$) δ: 8.10–7.12(16H, m) 6.88(0.65H, d, J=4.6 Hz), 6.54(0.35H, s), 6.09(0.65H, d, J=4.6 Hz), 6.07 (0.35H, s), 5.22(0.65H, t, J=4.3 Hz), 5.16(0.35H, dd, J=5.0 Hz 6.7 Hz), 4.68–4.90(2H, m), 2.32–2.43(9H, m), 0.11 (3.15H s), 0.03(5.85H, s) α-anomer:β-anomer=65:35

Example 11

Preparation of 1,2,3-tri-O-acetyl-5-O-(4-chlorobenzoyl)-3-C-ethynyl-α,β-D-ribofuranose:

The 5-O-(4-chlorobenzoyl)-3-C-ethynyl-D-ribofuranose (1.00 g; 3.20 mmol) obtained in Example 6 was suspended in dichloromethane (15 ml). To the resultant solution was added triethylamine (1.30 g; 12.8 mmol). A solution (1 ml) of 4-dimethylaminopyridine (12 mg; 0.098 mmol) in dichloromethane was added thereto, and the mixture was cooled on ice. Subsequently, acetyl chloride (0.90 ml; 12.8 mmol) was added to the mixture, and the liquid temperature was returned to room temperature. The mixture was stirred for five hours. Dichloromethane (20 ml) and water (10 ml) were added to the reaction mixture, the mixture was stirred for 30 minutes, then phases were separated. The dichloromethane phase was sequentially washed with water, 15% aqueous ammonium chloride solution, then with 25% aqueous sodium chloride solution. The dichloromethane phase was dried over magnesium sulfate. After filtration, the filtrate was evaporated under reduced pressure. The residue was purified by silica gel column chromatography (ethyl acetate:n-hexane=2:3), yielding 1.23 g (yield: 88%) of the title compound as a colorless oily substance.

FAB-MS: addition of KI, 477 (M+K)$^+$ $^1$H-NMR(CDCl$_3$) δ: 7.99–8.05(2H, m), 7.42–7.99(2H, m), 6.52(0.6H, d, J=4.6 Hz), 6.14(0.4H, s), 5.81(0.4H, s), 5.74 (0.6H, d, J=4.4 Hz), 4.66–4.78(3H, m), 2.78(0.4H, s), 2.72 (0.6H, s), 2.04–2.14(9H, m) α-anomer:β-anomer=6:4

Example 12

Preparation of 5-O-(4-chlorobenzoyl)-3-C-ethynyl-1,2,3-tri-O-propionyl-α,β-D-ribofuranose:

To dichloromethane (12 ml) were added the 5-O-(4-chlorobenzoyl)-3-C-ethynyl-D-ribofuranose (1.00 g; 3.20 mmol) obtained in Example 6, 4-dimethylaminopyridine (12 mg; 0.10 mmol), and triethylamine (1.56 ml; 11.2 mmol). The mixture was cooled on ice. Subsequently, propionyl chloride (0.97 ml; 11.2 mmol) was added to the mixture, and the liquid temperature was returned to room temperature. The mixture was stirred for 40 minutes. Methanol (0.3 ml) was added to the reaction mixture, and the mixture was stirred for ten minutes. The solvent was evaporated under reduced pressure. Ethyl acetate (40 ml) and water (40 ml) were added to the residue, and phases were separated. The ethyl acetate phase was sequentially washed once with saturated sodium hydrogencarbonate solution and twice with water. The ethyl acetate phase was dried over magnesium sulfate. After filtration, the filtrate was evaporated under reduced pressure. The residue was purified by silica gel column chromatography (ethyl acetate:n-hexane=1:4), yielding 1.0 g (yield: 64%) of the title compound as a pale yellow oily substance.

FAB-MS: addition of KI, 519 (M+K)$^+$ $^1$H-NMR(DMSO-d$_6$) δ: 7.97–8.02(2H, m), 7.61–7.66(2H, m), 6.45(0.7H, d, J=4.4 Hz), 6.09(0.3H, s), 5.61(0.7H, d J=4.4 Hz), 5.58(0.3H, s), 4.55–4.70(3H, m), 4.07(0.3H, s), 3.99(0.7H, s), 2.32–2.45(6H, m), 1.00–1.07(9H, m) α-anomer:β-anomer=7:3

Example 13

Preparation of 5-O-(4-chlorobenzoyl)-3-C-ethynyl-1,2,3-tri-O-isobutyryl-α,β-D-ribofuranose:

To dichloromethane (12 ml) were added the 5-O-(4-chlorobenzoyl)-3-C-ethynyl-D-ribofuranose (1.0 g; 3.20 mmol) obtained in Example 6, 4-dimethylaminopyridine (12 mg; 0.10 mmol), and triethylamine (1.56 ml; 11.2 mmol). The mixture was cooled on ice. Subsequently, isobutyryl chloride (1.17 ml; 11.2 mmol) was added to the mixture, and the liquid temperature was returned to room temperature. The mixture was stirred for 40 minutes. Methanol (0.3 ml) was added to the reaction mixture, and the mixture was stirred for ten minutes. The solvent was evaporated under reduced pressure. Ethyl acetate (40 ml) and water (40 ml) were added to the residue, and phases were separated. The ethyl acetate phase was sequentially washed once with saturated sodium hydrogencarbonate solution and twice with water. The ethyl acetate phase was dried over magnesium sulfate. After filtration, the filtrate was evaporated under reduced pressure. The residue was purified by silica gel column chromatography (ethyl acetate:n-hexane=1:4), yielding 1.37 g (yield: 82%) of the title compound as a pale yellow oily substance.

FAB-MS: addition of KI, 561 (M+K)$^+$
$^1$H-NMR(CDCl$_3$) δ: 8.06–7.99(2H, m), 7.41–7.45(2H, m), 6.54(0.7H, d, J=4.6 Hz), 6.12(0.3H, d, J=1.2 Hz), 5.78(0.3H, d, J=1.2 Hz), 5.71(0.7H, d, J=4.6 Hz), 4.60–4.80(3H, m), 2.77(0.3H, s), 2.69(0.7H, s), 2.53–2.64(3H, m), 1.17–1.23 (18H, m)
α-anomer:β-anomer=7:3

Example 14

Preparation of 1,2,3-tri-O-benzoyl-5-O-(4-chlorobenzoyl)-3-C-ethynyl-α,β-D-ribofuranose:

To dichloromethane (12 ml) were added the 5-O-(4-chlorobenzoyl)-3-C-ethynyl-D-ribofuranose (1.0 g; 3.20 mmol) obtained in Example 6, 4-dimethylaminopyridine (12 mg; 0.10 mmol), and triethylamine (1.56 ml; 11.2 mmol). The mixture was cooled on ice. Subsequently, benzoyl chloride (1.30 ml; 11.2 mmol) was added to the mixture, and the liquid temperature was returned to room temperature. The mixture was stirred for 40 minutes. Methanol (0.3 ml) was added to the reaction mixture, and the mixture was stirred for ten minutes. The solvent was evaporated under reduced pressure. Ethyl acetate (40 ml) and water (40 ml) were added to the residue, and phases were separated. The ethyl acetate phase was sequentially washed once with saturated sodium hydrogencarbonate solution and twice with water. The ethyl acetate phase was dried over magnesium sulfate. After filtration, the filtrate was evaporated under reduced pressure. The residue was purified by silica gel column chromatography (ethyl acetate:n-hexane=1:4), yielding 1.77 g of a colorless oily substance. This product was dissolved in ethanol (20 ml) with the application of heat. The resultant ethanol solution was added to water (40 ml) with stirring at room temperature, and powder that precipitated was collected by filtration. The powder was dried under reduced pressure, to thereby obtain 1.63 g (yield 82%) of the title compound as white powder.

mp: 66°–68° C.
FAB-MS: addition of KI, 663 (M+K)$^+$
$^1$H-NMR(DMSO-d$_6$) δ: 7.27–8.08(19H, m), 6.91(0.7H, d, J=4.6 Hz), 6.61(0.3H, s), 6.13(0.3H, s), 6.12(0.7H, d, J=4.6 Hz), 5.16–5.27(1H, m), 4.70–4.95(2H, m), 4.40(0.3H, s), 4.11(0.7H, s)
α-anomer:β-anomer=7:3

Example 15

Preparation of 1,2,3,5-tetra-O-(4-chlorobenzoyl)-3-C-ethynyl-α,β-D-ribofuranose:

To dichloromethane (12 ml) were added the 5-O-(4-chlorobenzoyl)-3-C-ethynyl-D-ribofuranose (1.0 g; 3.20 mmol) obtained in Example 6, 4-dimethylaminopyridine (12 mg; 0.10 mmol), and triethylamine (2.0 ml; 12.8 mmol). The mixture was cooled on ice. Subsequently, 4-chlorobenzoyl chloride (1.59 ml; 12.8 mmol) was added to the mixture, and the liquid temperature was returned to room temperature. The mixture was stirred for 90 minutes. Water (15 ml) was added to the reaction mixture, the mixture was stirred for 30 minutes, then phases were separated. The dichloromethane phase was sequentially washed once with water, once with saturated sodium hydrogencarbonate solution, then once with water. The dichloromethane phase was dried over magnesium sulfate. After filtration, the filtrate was evaporated under reduced pressure. The residue was purified by silica gel column chromatography (dichloromethane). The solvent was evaporated, to thereby obtain 1.80 g (yield: 77%) of the title compound as colorless powder.

mp: 73°–78° C.
FAB-MS: addition of KI, 767 (M+K)$^+$
$^1$H-NMR(DMSO-d$_6$) δ: 7.41–8.02(16H, m), 6.88(0.7H, d, J=4.4 Hz), 6.61(0.3H, s) 6.12(1H, m), 5.30(0.7H, dd, J=3.7 Hz, 5.6 Hz), 5.20(0.3H, dd, J=4.2 Hz, 6.8 Hz), 4.7–4.9(2H, m), 4.38(0.3H, s), 4.13(0.7H, s) α-anomer:β-anomer=7:3

Example 16

Preparation of 5-O-(4-chlorobenzoyl)-3-C-ethynyl-1,2,3-tri-O-(4-toluoyl)-α,β-D-ribofuranose:

The 5-O-(4-chlorobenzoyl)-3-C-ethynyl-D-ribofuranose (1.0 g; 3.20 mmol) obtained in Example 6 was suspended in dichloromethane (15 ml), and thereto was added triethylamine (1.30 ml; 12.8 mmol). To the resultant solution was added a dichloromethane solution (1 ml) dissolving 4-dimethylaminopyridine (12 mg; 0.10 mmol). The mixture was cooled on ice. Subsequently, 4-toluoyl chloride (1.7 ml; 12.8 mmol) was added to the mixture, and the liquid temperature was returned to room temperature. The mixture was stirred for 3.5 hours. Water (30 ml) was added to the reaction mixture, and the mixture was stirred for 30 minutes. Dichloromethane (20 ml) and water (30 ml) were added, then phases were separated. The dichloromethane phase was sequentially washed once with 15% aqueous ammonium chloride solution and once with 25% sodium chloride solution. The dichloromethane phase was dried over magnesium sulfate. After filtration, the filtrate was evaporated under reduced pressure. The residue was purified by silica gel column chromatography (dichloromethane), yielding 1.04 g (yield: 50%) of the title compound as a colorless oily substance.

FAB-MS: addition of KI, 705 (M+K)$^+$
$^1$H-NMR (CDCl$_3$) δ: 7.00–8.08(16H, m), 6.94(0.7H, d, J=4.3 Hz), 6.61(0.3H, s), 6.32(0.3H, s), 6.10(0.7H, d, J=4.3 Hz), 4.76–5.06(3H, m), 2.94(0.3H, s), 2.79(0.7H, s), 2.35–2.45(9H, m)
α-anomer:β-anomer=7:3

Example 17

Preparation of 5-O-(4-chlorobenzoyl)-3-C-ethynyl-1,2,3-tri-O-(4-nitrobenzoyl)-α,β-D-ribofuranose:

The 5-O-(4-chlorobenzoyl)-3-C-ethynyl-D-ribofuranose (1.0 g; 3.20 mmol) obtained in Example 6 was suspended in dichloromethane (15 ml). To the resultant suspension was added triethylamine (2.40 ml; 17.2 mmol), 4-Dimethylaminopyridine (12 mg; 0.10 mmol) was added thereto and the mixture was cooled on ice. Subsequently, 4-nitrobenzoyl chloride (2.38 g; 12.8 mmol) was added to the mixture, and the liquid temperature was returned to room temperature. The mixture was stirred for 2 hours. Water (15 ml) was added to the reaction mixture, and the mixture was stirred for 30 minutes. Dichloromethane (20 ml) and water (30 ml) were added, then phases were separated. The dichloromethane phase was sequentially washed with water, saturated aqueous sodium hydrogencarbonate solution, and water, then dried over magnesium sulfate. After filtration, the filtrate was evaporated under reduced pressure. The residue was purified by silica gel column chromatography (dichloromethane), yielding 1.38 g (yield: 84%) of the title compound as pale yellow powder.

mp: 97°–103° C.

FAB-MS: addition of KI, 798 (M+K)$^+$
$^1$H-NMR(DMSO-d$_6$) δ: 7.52–8.41(16H, m), 6.93(0.7H, d, J=4.5 Hz), 6.77(0.3H, s) 6.25(0.7H d, J=4.5 Hz), 6.24(0.3H, s), 5.29–5.45(1H, m), 4.77–4.99(2H, m) 4.53(0.3H, s) 4.18 (0.7H, s)
α-anomer:β-anomer=7:3

Example 18

Preparation of 5-O-(4-chlorobenzoyl)-1,2,3-tri-O-ethoxycarbonyl-3-C-ethynyl-α,β-D-ribofuranose:

The 5-O-(4-chlorobenzoyl)-3-C-ethynyl-D-ribofuranose (1.0 g; 3.20 mmol) obtained in Example 6 was suspended in dichloromethane (12 ml). To the resultant suspension were added 4-dimethylaminopyridine (12 mg; 0.098 mmol) and triethylamine (1.56 ml; 11.2 mmol). The mixture was cooled on ice. Ethyl chlorocarbonate (1.07 ml; 11.2 mmol) was added thereto and the liquid temperature was returned to room temperature. The mixture was stirred for one hour. The solvent was evaporated under reduced pressure. Ethyl acetate (40 ml) and water (40 ml) were added to the residue, then phases were separated. The ethyl acetate phase was washed once with saturated aqueous sodium hydrogencarbonate solution, then dried over magnesium sulfate. After filtration, the filtrate was evaporated under reduced pressure. The residue was purified by silica gel column chromatography (ethyl acetate:n-hexane=1:3), yielding 1.42 g (yield: 84.0%) of the title compound as a colorless oily substance.
FAB-MS: addition of KI, 567 (M+K)$^+$
$^1$H-NMR(CDCl$_3$) δ: 8.03(1.1H, d, J=8.8 Hz), 8.00(0.9H, d, J=8.8 Hz), 7.43(1.1H, d, J=8.8 Hz), 7.42(0.9H, d, J=8.8 Hz), 6.46(0.45H, d, J=4.4 Hz), 6.15(0.55H, d, J=1.5 Hz), 5.70 (0.55H, d, J=1.5 Hz), 5.61(0.45H, d, J=4.4 Hz), 4.63–4.86 (3H, m), 4.21–4.31(6H, m), 2.84(0.55H, S), 2.77(0.45H, s), 1.30–1.35(9H, m)
α-anomer:β-anomer=45:55

Referential Example 1

Preparation of 1-[2,3,5-O-tri-(4-chlorobenzoyl)-3-C-(2-trimethylsilylethynyl)-β-D-ribofuranosyl]uracil:

Uracil (506 mg; 4.5 mmol), ammonium sulfate (16 mg; 0.12 mmol), and hexadimethyldisilazane (4.5 ml) were refluxed for one hour until uracil has dissolved to make a clear solution under nitrogen atmosphere. The reaction mixture was left to cool to room temperature. Subsequently, the solvent was evaporated under reduced pressure, and the residue was co-evaporated twice with toluene. An acetonitrile solution (9 ml) of the 5-O-(4-chlorobenzoyl)-3-C-(2-trimethylsilyl-ethynyl)-D-ribofuranose (900 mg; 1.12 mmol) obtained in Example 5 was added to the resultant oily matter, i.e., 2,4-bis-trimethylsilyluracil. Trimethylsilyltrifluoromethyl methanesulfonate (1.32 ml; 6.62 mmol) was added at 0° C. The mixture was stirred for 69 hours at room temperature. The reaction mixture was poured into an saturated aqueous sodium hydrogencarbonate solution (20 ml) with cooling. The reaction mixture was brought to dryness under reduced pressure. Subsequently, ethyl acetate (40 ml) was added, and insoluble matter was removed by filtration. The filtrate was washed with water (40 ml×3), and then dried over magnesium sulfate. The filtrate was evaporated under reduced pressure, and the residue was crystallized from isopropyl ether. The crystals that precipitated were collected by filtration, to thereby obtain 601 mg (yield: 71%) of the title compound.
mp: 107°–109° C.
FAB-MS: addition of KI, 721 (M+K)$^+$
$^1$H-NMR(DMSO-d$_6$) δ: 11.57(1H, s), 8.05(2H, d, J=8.3 Hz), 7.95(2H, d, J=8.5 Hz), 7.92(2H, d, J=8.5 Hz), 7.84(1H, d, J=8.1 Hz), 7.54–7.65(6H, m), 6.25(1H, d, J=4.2 Hz), 5.99 (1H, d, J=4.2 Hz), 5.78(1H, d, J=8.1 Hz), 5.07–5.10 (1H, m), 4.92(1H, dd, J=4.0 Hz, 6.0 Hz), 4.87(1H, dd, J=6.0 Hz, 12.2 Hz), 0.12(9H, s)

Referential Example 2

Preparation of 1-(3-C-Ethynyl-β-D-ribofuranosyl)uracil:
The 1-[2,3,5-O-tri-(4-chlorobenzoyl)-3-C-(2-trimethylsilylethynyl)-β-D-ribofuranosyl]uracil (100 mg; 0.13 mmol) obtained in Referential Example 1 was dissolved in methanol (1.3 ml). Triethylamine (0.65 ml; 4.66 mmol) was added thereto with stirring at room temperature, and the mixture was stirred for 48 hours at 50° C. Acetic acid (0.01 ml) was added, and the reaction mixture was concentrated. The residue was dissolved in methanol (0.2 ml), and crystallized from chloroform (4.0 ml). The crystals that precipitated were collected by filtration, to thereby obtain 30 mg (yield: 85%) of the title compound as white powder.
mp: 226°–228° C.
FAB-MS(negative): 267 (M–H)$^-$
$^1$H-NMR(DMSO-d$_6$) δ: 11.35(1H, brs), 7.99(1H, d, J=8.2 Hz), 5.93(1H, d, J=8.2 Hz), 5.86(1H, d, J=6.7 Hz, ) 5.83(1H, d, J=7.3 Hz), 5.69(1H, d, J=8.2 Hz), 5.13(1H, t, J=4.5 Hz), 4.18(1H, dd, J=7.3 Hz, 6.7 Hz), 3.90–3.88(1H, m), 3.74–3.60(2H, m), 3.55(1H, s)

Referential Example 3

Preparation of 1-[2,3,5-O-tri-(4-chlorobenzoyl)-3-C-(2-trimethylsilylethynyl)-β-D-ribofuranosyl]cytosine Cytosine (670 mg; 6.0 mmol), ammonium sulfate (21 mg; 0.16 mmol), and hexamethyldisilazane (6.0 ml) were refluxed for one hour until cytosine was dissolved to make a clear solution under nitrogene atomosphere. The reaction mixture was left to cool to room temperature. Subsequently, the solvent was evaporated under reduced pressure, and the residue was co-evaporated twice with toluene. The 5-O-(4-chlorobenzoyl)-3-C-(2-trimethylsilylethynyl)-D-ribofuranose (1.20 g; 1.5 mmol) obtained in Example 5 anhydrous acetonitrile (12 ml) was added to the resultant solid matter (i.e., 2,4-bis-trimethylsilylcytosine), and the mixture was stirred at room temperature until a clear solution was obtained. The reaction mixture was then cooled to 0° C. Stannic chloride (12 ml; 7.5 mmol) was added and the mixture was stirred for 40 hours at room temperature. The resultant reaction mixture was added to a saturated aqueous sodium hydrogencarbonate solution (32 ml) while being cooled on ice. The reaction mixture was concentrated to dryness under reduced pressure. Ethyl acetate was added to the residue, and the insoluble matter was removed by filtration. The filtrate was washed with water three times, and then dried over magnesium sulfate. The solvent was evaporated, and the residue was crystallized from isopropyl ether (20 ml). The crystals that precipitated were collected by filtration, to thereby obtain 460 mg (yield: 41%) of the title compound.
mp: 131°–133° C.
FAB-MS: 754 (M+H)$^+$
$^1$H-NMR(DMSO-d$_6$) δ: 8.05(2H, d, J=8.5 Hz), 7.88–7.95 (4H, m), 7.79(1H, d, J=7.6 Hz), 7.63(2H, d, J=8.3 Hz), 7.58(2H, d, J=8.3 Hz), 7.53(2H, d, J=8.3 Hz), 7.39–7.42(2H, br), 6.27(1H, d, J=3.9 Hz), 5.93(1H, d, J=3.9 Hz), 5.84(1H, d, J=7.6 Hz), 5.04–5.06(1H, m), 4.91(1H, dd, J=4.1 Hz. 12.0 Hz), 4.77–4.81(1H, m), 0.11(9H, s)

Referential Example 4

Preparation of 1-(3-C-Ethynyl-β-D-ribofuranosyl)-cytosine:

The 1-[2,3,5-O-tri-(4-chlorobenzoyl)-3-C-(2-trimethylsilylethynyl)-β-D-ribofuranosyl]cytosine (95 mg) obtained in Referential Example 3 was dissolved in methanol (1.3 ml). Triethylamine (0.65 ml; 4.65 mmol) was added thereto with stirring at room temperature, and the mixture was stirred for 30 hours at 50° C. The reaction mixture was concentrated. The residue was dissolved in methanol (0.2 ml), and crystallized from chloroform (4.0 ml). The crystals that precipitated were collected by filtration, to thereby obtain 29.7 mg (yield: 88%) of the title compound as white powder.

mp: 233°~235° C.
FAB-MS(negative): 266 (M–H)⁻
$^1$H-NMR(DMSO-d$_6$) δ: 7.81(1H, d, J=7.6 Hz), 7.21(1H, brs), 7.17(brs, 1H), 5.83(1H, d, J=6.6 Hz), 5.73–5.79(3H, m), 5.02(1H, t, J=4.9 Hz), 4.11(1H, t, J=6.6 Hz), 3.85–3.87 (1H, m), 3.65–3.69(2H, m), 3.51(1H, s)

Referential Example 5

Preparation of 1-[5-O-(4-chlorobenzoyl)-2,3-di-O-isobutyryl-3-C-(2-trimethylsilylethynyl)-β-D-ribofuranosyl]uracil:

The 5-O-(4-chlorobenzoyl)-1,2,3-tri-O-isobutyryl-3-C-(2-trimethylsilylethynyl)-α,β-D-ribofuranose (298 mg; 0.05 mmol) obtained in Example 8 was dissolved in acetonitrile (0.94 ml). A solution (1.06 ml) of 2,4-bis-trimethylsilyl uracil (256 mg; 1.0 mmol) in acetonitrile was added thereto under nitrogen atmosphere. After the mixture was cooled on ice, stannic chloride (177 μl; 1.50 mmol) was added, and the mixture was stirred for 20 hours at 30° C. The reaction mixture was added dropwise to 6% aqueous sodium hydrogencarbonate solution (10 ml), and the solvent was evaporated. Chloroform (50 ml) was added to the residue, and the mixture was extracted. The chloroform phase was washed once with saturated aqueous sodium hydrogencarbonate solution, then once with saturated aqueous sodium chloride solution, and then dried over magnesium sulfate. After filtration, the filtrate was evaporated under reduced pressure, and the residue was purified by silica gel column chromatography (ethyl acetate:n-hexane=1:3). The resultant oily substance was dissolved in isopropyl ether. n-Heptane was added, and crystals that precipitated were collected by filtration. The crystals were dried under reduced pressure, to thereby obtain 228 mg (yield: 73.7%) of the title compound as white powder.

mp: 160°~161° C.
FAB-MS: 619 (M+H)⁺
$^1$H-NMR(DMSO-d$_6$) δ: 11.51(1H, s), 8.02(2H, d, J=8.5 Hz), 7.75(1H, d, J=8.3 Hz), 7.63(2H, d, J=8.5 Hz), 6.01(1H, d, J=5.4 Hz), 5.72(1H, d, J=8.3 Hz), 5.63(1H, d, J=5.4 Hz), 4.64–4.76(3H, m), 2.60–2.68(2H, m), 1.08–1.13(12H, m), 0.06(9H, m)

Referential Example 6

Preparation of 1-[5-O-(4-chlorobenzoyl)-3-C-(2-trimethylsilylethynyl)-2,3-di-O-(4-toluoyl)-β-D-ribofuranosyl]uracil:

The 5-O-(4-chlorobenzoyl)-1,2,3-tri-O-(4-toluoyl)-3-C-(2-trimethylsilylethynyl)-α,β-D-ribofuranose (370 mg; 0.50 mmol) obtained in Example 10 was dissolved in acetonitrile (0.45 ml). A solution (1.55 ml) of 2,4-bis-trimethylsilyl uracil (257 mg; 1.0 mmol) in acetonitrile was added thereto under nitrogen atmosphere. After the mixture was cooled on ice, stannic chloride (177 μl; 1.50 mmol) was added, and the mixture was stirred for 20 hours at 30° C. The reaction mixture was added dropwise to 6% aqueous sodium hydrogencarbonate solution (10 ml), and the solvent was evaporated. Chloroform (30 ml) was added to the residue, and the mixture was extracted. The chloroform phase was dried over magnesium sulfate. After filtration, the filtrate was evaporated under reduced pressure, and the residue was purified by silica gel column chromatography (chloroform: ethyl acetate=15:1). The residue was dissolved in ethyl acetate, with n-heptane being added, and crystals that precipitated were collected by filtration. The crystals were dried under reduced pressure, to thereby obtain 317 mg (yield: 88.6%) of the title compound as white powder.

mp: 105°–107° C.
FAB-MS: addition of KI, 714 (M+K)⁺
$^1$H-NMR(DMSO-d$_6$) δ: 11.55(1H, s), 8.05(2H, d, J=8.3 Hz), 7.78–7.86(5H, m), 7.62(2H, d, J=8.5 Hz), 7.33(2H, d, J=8.1 Hz), 7.25(2H, d, J=8.1 Hz), 6.21(1H, d, J=4.4 Hz), 5.94(1H, d, J=4.4 Hz), 5.77(1 H, d, J=8.1 Hz), 4.75–5.03(3H, m), 2.39(3H, s), 2.33(3H, s), 0.10(9H, s)

Referential Example 7

Preparation of 1-[2,3-di-O-acetyl-5-O-(4-chlorobenzoyl)-3-C-ethynyl-β-D-ribofuranosyl]uracil:

The 1,2,3-tri-O-acetyl-5-O-(4-chlorobenzoyl)-3-C-ethynyl-α,β-D-ribofuranose (439 mg; 1.0 mmol) obtained in Example 11 was dissolved in acetonitrile (4.65 ml). A solution (3.35 ml) of 2,4-bis-trimethylsilyl uracil (513 mg; 2.0 mmol) in acetonitrile was added thereto under nitrogen atmosphere. After the mixture was cooled on ice, stannic chloride (118 μl; 1.0 mmol) was added, and the mixture was stirred for 20 hours at 30° C. The reaction mixture was added dropwise to aqueous 0.10M sodium hydrogencarbonate solution (25 ml), and extracted with ethyl acetate (30 ml×3). The ethyl acetate extracts were combined, and the solvent was evaporated under reduced pressure. Aqueous 0.10 M sodium hydrogencarbonate solution (25 ml) was added to the residue, and the mixture was extracted with ethyl acetate (30 ml). The ethyl acetate phase was dried over magnesium sulfate. After filtration, the filtrate was evaporated under reduced pressure, and the residue was purified by silica gel column chromatography (dichloromethane:methanol=97:3). The resultant substance was crystallized from isopropyl ether, to thereby obtain 50 mg (yield: 10%) of the title compound as white powder.

mp: 218°~219° C.
FAB-MS: 491 (M+H)⁺
$^1$H-NMR(DMSO-d$_6$) δ: 11.50(1H s), 7.99(2H, d, J=6.6 Hz), 7.75(1H, d, J=8.3 Hz),7.63(2H, d, J=6.6 Hz),6.03(1H, d, J=5.8 Hz), 5.73(1H, d, J=8.3 Hz), 5.62(1H, d, J=5.8 Hz), 4.65–4.78(3H, m), 4.07(1H, s), 2.15(3H, s), 2.10(3H, s)

Referential Example 8

Preparation of 1-[5-O-(4-chlorobenzoyl)-3-C-ethynyl-2,3-di-O-propionyl-β-D-ribofuranosyl]uracil:

The 5-O-(4-chlorobenzoyl)-3-C-ethynyl-1,2,3-tri-O-propionyl-α,β-D-ribofuranose (393 mg; 0.80 mmol) obtained in Example 12 was dissolved in acetonitrile (3.72 ml). A solution (2.68 ml) of 2,4-bis-trimethylsilyl uracil (410 mg; 1.60 mmol) in acetonitrile was added thereto under nitrogen atmosphere. After the mixture was cooled on ice, stannic chloride (94 μl; 0.80 mmol) was added, and the mixture was stirred for 20 hours at 30° C. The reaction mixture was added dropwise to aqueous 0.19M sodium hydrogencarbonate solution (20 ml), and the mixture was extracted with ethyl acetate (30 ml×3). The ethyl acetate extracts were combined, washed with saturated aqueous sodium hydrogencarbonate solution, and dried over magnesium sulfate. After filtration, the filtrate was evaporated under reduced pressure, and the residue was purified by silica gel column chromatography (ethyl acetate:n-hexane= 1:1). The resultant crude crystals were dissolved in ethyl acetate, with n-heptane being added, and crystals that precipitated were collected by filtration. The crystals were dried under reduced pressure, to thereby obtain 83 mg (yield: 20%) of the title compound as white powder.
mp: 208°~210° C.
FAB-MS: 519 (M+H)$^+$
$^1$H-NMR(DMSO-d$_6$) δ: 11.51(1H, s), 7.99(2H, d, J=8.5 Hz), 7.74(1H, d, J=8.1 Hz), 7.64(2H, d, J=8.5 Hz), 6.02(1H, d, J=5.4 Hz), 5.74(1H d, J=8.1 Hz), 5.61(1H, d J=5.4 Hz), 4.66–4.78(3H, m), 4.07(1H, s), 2.33–2.46(4H, m), 1.04(3H, t, J=7.6 Hz), 1.03(3H, t, J=7.9 Hz)

Referential Example 9

Preparation of 1-[5-O-(4-chlorobenzoyl)-3-C-ethynyl-2, 3-di-O-isobutyryl-β-D-ribofuranosyl]uracil:

The 5-O-(4-chlorobenzoyl)-3-C-ethynyl-1,2,3-tri-O-isobutyryl-α,β-D-ribofuranose (523 mg; 1.0 mmol) obtained in Example 13 was dissolved in acetonitrile (4.65 ml). A solution (3.35 ml) of 2,4-bis-trimethylsilyl uracil (513 mg; 2.0 mmol) in acetonitrile was added thereto under nitrogen atmosphere. After the mixture was cooled on ice, stannic chloride (354 μl; 3.0 mmol) was added, and the mixture was stirred for 20 hours at 30° C. The reaction mixture was added dropwise to aqueous 0.71M sodium hydrogencarbonate solution (20 ml), and the mixture was extracted with ethyl acetate (30 ml×3). The ethyl acetate extract were combined, washed with saturated aqueous sodium chloride solution, and dehydrated with magnesium sulfate. After filtration, the filtrate was evaporated under reduced pressure, and the residue was purified by silica gel column chromatography (dichloromethane:methanol=30:1). The resultant crude crystals were dissolved in ethyl acetate, with n-heptane being added, and crystals that precipitated were collected by filtration. The crystals were dried under reduced pressure, to thereby obtain 429 mg (yield: 78%) of the title compound as white powder.
mp: 198°~199° C.
FAB-MS: 547 (M+H )$^+$
$^1$H-NMR(DMSO-d$_6$) δ: 11.50(1H, s), 8.00(2H, d, J=8.8 Hz), 7.75(H, d, J=8.1 Hz), 7.64(2H, d, J=8.8 Hz), 6.0(1H, d, J=5.6 Hz), 5.74(1H, d, J=8.1 Hz), 5.60(1H, d, J=5.6 Hz) 4.66–4.80 (3H, m), 4.06(1H, s), 2.55–2.69(2H, m), 1.08(12H, m)

Reference Example 10

Preparation of 1-[2,3-di-O-benzoyl-5-O-(4-chlorobenzoyl)-3-C-ethynyl-β-D-ribofuranosyl]uracil:

The 1,2,3-tri-O-benzoyl-5-O-(4-chlorobenzoyl)-3-C-ethynyl-α,β-D-ribofuranose (625 mg; 1.0 mmol) obtained in Example 14 was dissolved in acetonitrile (0.98 ml). A solution (3.02 ml) of 2,4-bis-trimethylsilyl uracil (513 mg; 2.0 mmol) in acetonitrile was added thereto under nitrogen atmosphere. After the mixture was cooled on ice, stannic chloride (354 μl; 3.0 mmol) was added, and the mixture was stirred for 20 hours at 30° C. The reaction mixture was added dropwise to aqueous 0.71M sodium hydrogencarbonate solution (20 ml), and washed with ethyl acetate (30 ml×3). The ethyl acetate extracts were combined, washed with saturated aqueous sodium chloride solution, and dried over magnesium sulfate. After filtration, the filtrate was evaporated under reduced pressure. The residue was purified by silica gel column chromatography (ethyl acetate:n-hexane= 1:1). The resultant crude crystals were dissolved in ethyl acetate, with n-heptane being added, and the crystals that precipitated were collected by filtration. The crystals were dried under reduced pressure, to thereby obtain 414 mg (yield: 67%) of the title compound as white powder.
mp: 158°~160° C.
FAB-MS: 615 (M+H)$^+$
$^1$H-NMR(DMSO-d$_6$) δ: 11.54(1H, s) 7.43–8.05(15H, m), 6.26(1H, d, J=4.9 Hz), 5.98(1H, d, J=4.9 Hz), 5.80(1H, d, J=8.3 Hz), 4.79–5.07(3H, m) 4.21(1H, s)

Referential Example 11

Preparation of 1-[5-O-(4-chlorobenzoyl)-3-C-ethynyl-2, 3-di-O-(4-toluoyl)-β-D-ribofuranosyl]uracil:

The 5-O-(4-chlorobenzoyl)-3-C-ethynyl-1,2,3-tri-O-(4-toluoyl)-α,β-D-ribofuranose (667 mg; 1.0 mmol) obtained in Example 16 was dissolved in acetonitrile (0.98 ml). A solution (3.02 ml) of 2,4-bis-trimethylsilyl uracil (513 mg; 2.0 mmol) in acetonitrile was added thereto under nitrogen atmosphere. After the mixture was cooled on ice, stannic chloride (354 μl; 3.0 mmol) was added, and the mixture was stirred for 20 hours at 30° C. The reaction mixture was added dropwise to aqueous 0.48M sodium hydrogencarbonate solution (30 ml), and the mixture was extracted with ethyl acetate (30 ml×2) and then with chloroform (30 ml×2). The organic extracts were combined and dried over magnesium sulfate. After filtration, the filtrate was evaporated under reduced pressure, and the residue was purified by silica gel column chromatography (ethyl acetate:n-hexane=1:1), to thereby obtain 614 mg (yield: 96%) of the title compound as white powder.
mp: 125°~127° C.
FAB-MS: 643 (M+H)$^+$
$^1$H-NMR(CDCl$_3$) δ: 7.10–8.07(15H, m), 6.35(1H, d, J=5.0), 5.77–5.96(2H, m), 4.84–4.94(2H, m), 2.90(1H, S), 2.44(3H, s), 2.36(3H, s)

Referential Example 12

Preparation of 1-[2,3,5-tri-O-(4-chlorobenzoyl)-3-C-ethynyl-β-D-ribofuranosyl]uracil:

The 1,2,3,5-tetra-O-(4-chlorobenzoyl)-3-C-ethynyl-α, β-D-ribofuranose (728 mg; 1.0 mmol) obtained in Example 15 was dissolved in acetonitrile (0.98 ml). A solution (3.02 ml) of 2,4-bis-trimethylsilyl uracil (513 mg; 2.0 mmol) in acetonitrile was added thereto under nitrogen atmosphere. After the mixture was cooled on ice, stannic chloride (354 μl; 3.0 mmol) was added, and the mixture was stirred for 20 hours at 30° C. The reaction mixture was added dropwise to aqueous 0.48M sodium hydrogencarbonate solution (30 ml), and the mixture was extracted with ethyl acetate (30 ml×6). The ethyl acetate extracts were combined and dried over magnesium sulfate. After filtration, the filtrate was evaporated under reduced pressure, and the residue was purified by silica gel column chromatography (ethyl acetate: n-hexane=1:1). The resultant substance was crystallized from isopropyl ether, to thereby obtain 425 mg (yield: 62%) of the title compound as crystals.
mp: 115°~117° C.
FAB-MS: 683 (M+H)$^+$
$^1$H-NMR(DMSO-d$_6$)δ:11.52(1H, brs), 7.83–8.04(7H, m), 7.56–7.66(6H, m), 6.26(1H, d, J=5.1 Hz), 6.00(1H, d, J=5.1 Hz), 5.79(1H, d, J=8.3 Hz), 5.07(1H, m), 4.93(1H, m), 4.82(1H, m)4.21(1H, s)

Reference Example 13

Preparation of 1-[5-O-(4-chlorobenzoyl)-3-C-ethynyl-2, 3-di-O-(4-nitrobenzoyl)-β-D-ribofuranosyl]uracil:

The 5-O-(4-chlorobenzoyl)-3-C-ethynyl-1,2,3-tri-O-(4-nitrobenzoyl)-α,β-D-ribofuranose (760 mg; 1.0 mmol) obtained in Example 17 was dissolved in acetonitrile (0.98 ml). A solution (3.02 ml) of 2,4-bis-trimethylsilyl uracil (513 mg; 2.0 mmol) in acetonitrile was added thereto under nitrogen atmosphere. After the mixture was cooled on ice, stannic chloride (354 μl; 3.0 mmol) was added, and the mixture was stirred for 20 hours at 30° C. The reaction mixture was added dropwise to aqueous 0.48M sodium hydrogencarbonate solution (30 ml), and the mixture was extracted with a solvent mixture of ethyl acetate/tetrahydrofuran (30 ml×4). The organic extracts were combined and dried over magnesium sulfate. After filtration, the filtrate was evaporated under reduced pressure, and the residue was purified by silica gel column chromatography (chloroform:methanol=20:1). Crystallization from n-heptane afforded 84 mg (yield: 12%) of the title compound as pale yellow powder.
mp: 226°~228° C.
FAB-MS: 705 (M+H)$^+$
$^1$H-NMR(DMSO-d$_6$) δ: 11.53(1H, brs), 8.38–8.18(8H, m), 8.03 (2H, dd, J=1.8 Hz, 6L7 Hz), 7.88 (1H, d, J=8.3 Hz), 7.63 (2H, dd, J=1.8 Hz, 6.7 Hz), 6.33 (1H, d, J=5.6 Hz), 6.11(1H, d, J=5.6 Hz), 5.79(1H, d, 8.3 Hz), 5.16(1H, dd, J=4.1 Hz, 6.8 Hz), 4.95(1H, dd, J=4.1 Hz, 12.0Hz), 4.85(1H, dd, J=6.8 Hz, 12.0 Hz), 4.26(1H, s)

Referential Example 14

Preparation of 1-[5-O-(4-chlorobenzoyl)-2,3-di-O-ethoxycarbonyl-3-C-ethynyl-β-D-ribofuranosyl]uracil:

The 5-O-(4-chlorobenzoyl)-1,2,3-tri-O-ethoxycarbonyl-3-C-ethynyl-α,β-D-ribofuranose (265 mg; 0.50 mmol) obtained in Example 18 was dissolved in acetonitrile (0.94 ml). A solution (1.06 ml) of 2,4-bis-trimethylsilyl uracil (256 mg; 1.0 mmol) in acetonitrile was added thereto under nitrogen atmosphere. After the mixture was cooled on ice, stannic chloride (177 μl; 1.5 mmol) was added, and the mixture was stirred for 3 hours at 30° C. The reaction mixture was added dropwise to aqueous 6% sodium hydrogencarbonate solution (10 ml), and the solvent was evaporated. The residue was extracted with chloroform (30 ml). The chloroform extract was washed with saturated aqueous sodium chloride solution, and then dried over magnesium sulfate. After filtration, the filtrate was evaporated under reduced pressure, and the residue was purified by silica gel column chromatography (n-hexane:ethyl acetate=1:1). Isopropyl ether was added to the resultant oily substance. Crystals that precipitated were collected by filtration, yielding 155 mg (yield: 56.3%) of the title compound as white powder.
mp: 154°~156° C.
FAB-MS: 551 (M+H)$^+$
$^1$H-NMR(DMSO-d$_6$) δ: 11.53(1H, s), 7.99(2H, d, J=8.5 Hz), 7.77(1H, d, J=8.3 Hz), 7.63(2H, d, J=8.5 Hz), 6.07(1H, d, J=6.1 Hz), 5.73(1H, d, J=8.3 Hz), 5.60(1H, d, J=6.1 Hz), 4.65–4.82(3H, m), 4.15–4.24(3H, m), 1.25(3H, s), 1.21(3H, s)

Referential Example 15

In a manner similar to that described in Referential Example 2, 1-(3-C-ethynyl-β-D-ribofuranosyl)uracil was prepared by use of the compounds of Referential Examples 5 through 14.

Referential Example 16

Preparation of 1-[5-O-(4-chlorobenzoyl)-2,3-di-O-isobutyryl-3-C-(2-trimethylsilylethynyl)-β-D-ribofuranosyl]cytosine:

The 5-O-(4-chlorobenzoyl)-1,2,3-tri-O-isobutyryl-3-C-(2-trimethylsilylethynyl)-α,β-D-ribofuranose (595 mg; 1.00 mmol) obtained in Example 8 was dissolved in acetonitrile (4 ml), 2,4-bis-Trimethylsilyl cytosine (511 mg; 2.0 mmol) was added thereto. After the mixture was cooled on ice, stannic chloride (354 μl; 3.00 mmol) was added, and the mixture was stirred for 20 hours at 30° C. The reaction mixture was added dropwise to 6% aqueous sodium hydrogencarbonate solution (20 ml), and the solvent was evaporated. Chloroform (50 ml) was added to the residue, and the mixture was extracted. The chloroform extract was washed once with saturated aqueous sodium hydrogencarbonate solution then once with saturated aqueous sodium chloride solution, and then dried over magnesium sulfate. After filtration, the filtrate was evaporated under reduced pressure, and the residue was purified by silica gel column chromatography (chloroform:methanol=20:1). The resultant oily substance was crystallized from isopropyl ether/n-heptane, and crystals that precipitated were collected by filtration. The crystals were dried under reduced pressure, to thereby obtain 392 mg (yield: 63.4%) of the title compound as white powder.
mp: 97°~99° C.
FAB-MS: 618 (M+H)$^+$
$^1$H-NMR(DMSO-d$_6$) δ: 8.03(2H, d, J=8.4 Hz), 7.68(1H, d, J=7.6 Hz), 7.63(2H, d, J=8.4 Hz), 7.35(1H, brs), 7.33(1H, brs), 6.08(1H, d, J=5.0 Hz), 5.78(1H d J=7.6 Hz), 5.61(1H, d, J=5.0 Hz) 4.64–4.76(3H, m), 2.52–2.67(2H, m), 1.08–1.12(12H, m), 0.07(9H, S)

Referential Example 17

Preparation of 1-[5-O-(4-chlorobenzoyl)-3-C-(2-trimethylsilylethynyl)-2,3-di-O-(4-toluoyl)-β-D-ribofuranosyl]cytosine:

The 5-O-(4-chlorobenzoyl)-3-C-(2-trimethylsilylethynyl)-1,2,3-tri-O-(4-toluoyl)-α,β-D-ribofuranose (370 mg; 0.50 mmol) obtained in Example 10 was dissolved in acetonitrile (2 ml), 2,4-bis-Trimethylsilyl cytosine (255 mg; 1.00 mmol) was added thereto. After the mixture was cooled on ice, stannic chloride (177 μl; 1.5 mmol) was added, and the mixture was stirred for 20 hours at 30° C. The reaction mixture was added dropwise to 6% aqueous sodium hydrogencarbonate solution (10 ml), and the solvent was evaporated. The residue was extracted with chloroform (30 ml). The chloroform extract was dried over magnesium sulfate. After filtration, the filtrate was evaporated under reduced pressure, and the residue was purified by silica gel column chromatography (chloroform:methanol=20:1). The resultant residue was crystallized from isopropyl ether/n-heptane, and crystals that precipitated were collected by filtration. The crystals were dried under reduced pressure, to thereby obtain 215 mg. (yield: 60.0%) of the title compound as white powder.
mp: 130°–132° C.
FAB-MS: addition of KI, 752 (M+K)$^+$
$^1$H-NMR(DMSO-d$_6$) δ: , 8.04–8.07(2H, m), 7.78–7.83(5H, m), 7.60–7.63(2H, m), 7.41 (1H, brs) 7.40(1H, brs), 7.30 (2H, d, J=8.1 Hz), 7.24(2H, d, J=8.1 Hz), 6.26(1H, d, J=3.9 Hz), 5.91(1H, d, J=3.9 Hz), 5.85(H, d, J=7.6 Hz), 4.75–5.01 (3H, m), 2.38(3H, s), 2.33(3H, s), 0.10(9H, s)

Reference Example 18

Preparation of 1-[5-O-(4-chlorobenzoyl)-3-C-ethynyl-2,3-di-O-isobutyryl-β-D-ribofuranosyl]cytosine The 5-O-(4-chlorobenzoyl)-3-C-ethynyl-1,2,3-tri-O-isobutyryl-α,β-D-ribofuranose (523 mg; 1.0 mmol) obtained in Example 13 was dissolved in acetonitrile (4 ml), 2,4-bis-Trimethylsilyl cytosine (306 mg; 1.2 mmol) was added thereto. After the mixture was cooled on ice, stannic chloride (117 μl; 1.5 mmol) was added, and the mixture was stirred for 20 hours at 30° C. The reaction mixture was added dropwise to aqueous 0.71M sodium hydrogencarbonate solution (20 ml), and the solvent was evaporated under reduced pressure. The residue was extracted with chloroform (30 ml×3). The chloroform extracts were combined, washed with saturated aqueous NaCl solution, and filtrate magnesium sulfate. After filtration, the solvent was evaporated under reduced pressure, and the residue was purified by silica gel column chromatography (chloroform:methanol=20:1). The resultant crude crystals were dissolved in methyl isobutyl ketone, with n-heptane being added, and crystals that precipitated were collected by filtration. The crystals were dried under reduced pressure, to thereby obtain 216 mg (yield: 54.2%) of the title compound as white powder.

mp: 106°–108° C.

FAB-MS: addition of KI, 584 (M+K)$^+$ $^1$H-NMR(DMSO-d$_6$) δ: 8.02(2H, d, J=8.9 Hz), 7.66(1H, d, J=7.6 Hz), 7.63(2H, d, J=8.9 Hz), 7.33(1H, brs), 7.37(1H, brs), 6.08(1H, d, J=5.3 Hz), 5.79(1H, d, J=7.6 Hz), 5.59(1H, d, J=5.3 Hz), 4.62–4.78(3H, m), 4.03(1H, s), 2.49–2.69(2H, m), 1.07–1.13(12H, m)

Referential Example 19

In a manner similar to that described in Referential Example 4, 1-(3-C-ethynyl-β-D-ribofuranosyl)cytosine was prepared by use of the compounds of Referential Examples 16 through 18.

Industrial Applicability

The compounds of the present invention are useful as intermediates in the industrial manufacture of 3'-C-substituted ribonucleoside derivatives which have excellent antitumor activities.

We claim:

1. A D-pentofuranose derivative represented by the following formula (1):

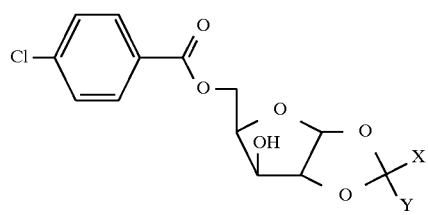

wherein each of X and Y represents a lower alkyl group and the sugar moiety represents xylose.

2. A D-pentofuranose derivative represented by the following formula (2):

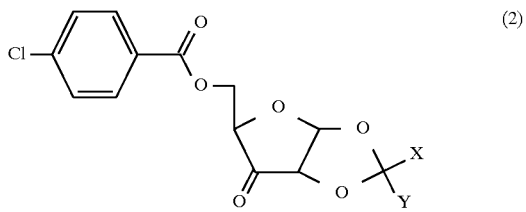

wherein each of X and Y represents a lower alkyl group.

3. A D-pentofuranose derivative represented by the following formula (3):

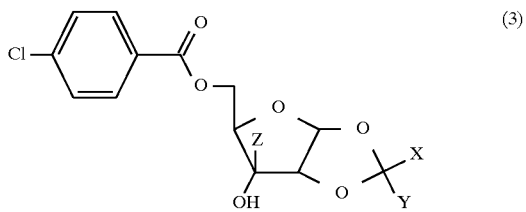

wherein each of X and Y represents a lower alkyl group, Z represents an ethynyl group which may be substituted by a trialkylsilyl group, and the sugar moiety represents ribose.

4. A D-pentofuranose derivative represented by the following formula (4):

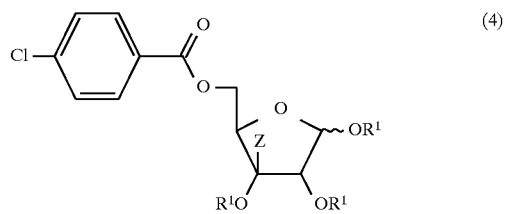

wherein R$^1$ represents a hydrogen atom, an aliphatic lower acyl group, a substituted or unsubstituted benzoyl group, or a lower alkyloxycarbonyl group, Z represents an ethynyl group which may be substituted by a trialkylsilyl group, and the sugar moiety represents ribose.

5. A process for preparing a D-pentofuranose derivative of the following formula (2):

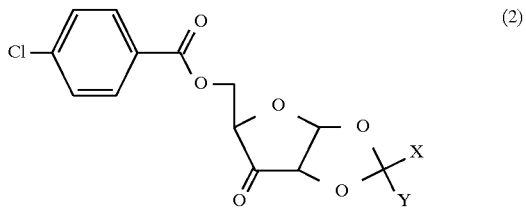

wherein each of X and Y represents a lower alkyl group, which process comprises oxidizing a D-pentofuranose derivative of the following formula (1):

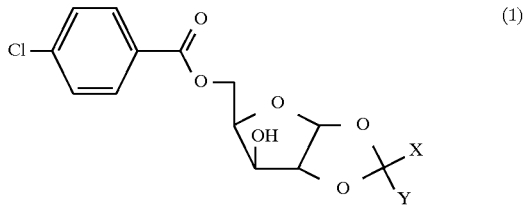

wherein each of X and Y represents a lower alkyl group and the sugar moiety represents xylose) with a hypochlorite in the presence of a catalytic amount of a compound of the following formula (5):

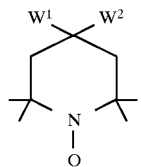

(5)

wherein each of $W^1$ and $W^2$, which may be identical to or different from each other, represents a hydrogen atom or a lower alkoxy group, or $W^1$ and $W^2$ may be linked to each other to represent an oxo group.

6. The process for preparing a D-pentofuranose derivative according to claim 5, wherein the hypochlorite is sodium hypochlorite or calcium hypochlorite.

* * * * *